United States Patent [19]

Hunter et al.

[11] 4,029,803

[45] June 14, 1977

[54] METHOD OF TREATMENT WITH 2-IMINOTHIAZOLIDINES AND THIAZOLINES

[75] Inventors: Norman R. Hunter, St. Norbert; Clarence S. Rooney, Beaconsfield; Joshua Rokach, Laval, all of Canada; Edward J. Cragoe, Jr., Lansdale, Pa.

[73] Assignee: Merck & Co., Inc., Rahway, N.J.

[22] Filed: May 3, 1976

[21] Appl. No.: 682,802

[52] U.S. Cl. .................................................. 424/270
[51] Int. Cl.² .................................... A61K 31/425
[58] Field of Search .................................... 424/270

[56] References Cited

OTHER PUBLICATIONS

Chem. Pharm. Bull. Tokyo, 14, 1201 (1966).
Chem. Abst., vol. 58, 11341g (1963).
J. Chem. Soc., 2943 (1955).
Chem. Abst., vol. 60, 7903d (1964).

*Primary Examiner*—Stanley J. Friedman
*Attorney, Agent, or Firm*—William H. Nicholson; Harry E. Westlake, Jr.

[57] ABSTRACT

A method of inhibiting indoleamine-N-methyl transferase comprises the administration to a host of a therapeutically effective amount of a 3-hydrocarbyl-2-imino-thiazolidine or thiazoline or a pharmaceutically acceptable salt thereof.

4 Claims, No Drawings

METHOD OF TREATMENT WITH 2-IMINOTHIAZOLIDINES AND THIAZOLINES

The present invention relates to novel and useful pharmaceutical compositions and a method of treatment. More specifically, it relates to compositions and a method for inhibiting indoleamine-N-methyl transferase by the administration of a 3-hydrocarbyl-2-iminothiazolidine or -thiazoline.

N,N-dimethyl indoleamines are generally psychotomimetic agents and some of these (e.g. dimethyl serotonin and dimethyl tryptamine) may be produced in excessive amounts by patients with mental aberrations (i.e. schizophrenia). Indoleamine-N-methyl transferase catalyzes the methylation steps in the biosynthesis of these compounds. Accordingly, inhibitors of this enzyme are of therapeutic value in the management of the body chemistry of patients having mental aberrations and in alleviating some symptoms of the disease.

It is an object of the present invention to provide compositions which inhibit indoleamine-N-methyl transferase. Another object is to provide a method of inhibiting transferase with relatively non-toxic materials. Other objects will become apparent as the description of the invention proceeds.

These objects are accomplished by the present invention which provides a method of inhibiting indoleamine-N-methyl transferase comprising the administration to a host of a therapeutically effective amount of a 3-hydrocarbyl-2-imino-thiazolidine or -thiazoline or a pharmaceutically acceptable salt thereof.

In a preferred embodiment of the present invention, the compound is 3-methyl-2-iminothiazolidine.

The compounds employed in the present invention have the following structural formula:

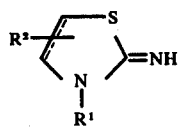

wherein
$R^1$ is $C_{1-2}$ alkyl, $C_3$-alkenyl, or $C_3$-alkynyl; and
$R^2$ is hydrogen, $C_{1-3}$ alkyl, or trifluoromethyl.

The compounds useful in the composition and method of treatment of this invention are known in the art, available commercially or may be prepared by well known prior art methods as, for example, by the procedures illustrated in *Chem. Pharm. Bull. Tokyo*, 14, 1201 (1966), *Chem. Abstr.*, 58, 11341g, and *J. Chem. Soc.*, 2943 (1955).

In general the daily dose can be from about 0.10 mg./kg. to about 100 mg./kg. per day and preferably from 1 mg./kg. to 10 mg./kg. per day, bearing in mind, of course, that in selecting the appropriate dosage in any specific case, consideration must be given to the patient's weight, general health, metabolism, age and other factors which influence response to the drug.

Another embodiment of this invention is the provision of pharmaceutical compositions in dosage unit form which comprise from about 5 mg. to 500 mg. of a compound of the above formulae.

The pharmaceutical compositions may be in a form suitable for oral use, for example, as tablets, solutions, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch or alginic acid; binding agents, for example starch, gelatin or acacia, and lubricating agents, for example magnesium stearate, stearic acid or talc. The tablets may be uncoated or they may be coated by known techniques to delay disintegration and adsorption in the gastro-intestinal tract and thereby provide a sustained action over a longer period.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is dissolved or mixed with an oil or aqueous medium, for example arachis oil, liquid paraffin, olive oil or water by itself.

Aqueous suspensions or solution containing the active compound in admixture with excipients are suitable for the manufacture of aqueous suspensions. Such excipients are suspending agents, for example sodium carboxymethyl cellulose, methylcellulose, hydroxypropylmethylcellulose, sodium alginate, polyvinylpyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxy-cetanol, or condensation products of ethylene oxide with partial esters derived from fatty acids and a hexitol, for example polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example ethyl or n-propyl, p-hydroxy benzoate, one or more coloring agents, one or more flavoring agents and one or more sweetening agents, such as sucrose, saccharin, or sodium or calcium cyclamate.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally occurring gums, for example gum acacia or gum tragacanth, naturally occurring phosphatides, for example soya bean lecithin, and esters of partial esters derived from fatty acids and hexitol anhydrides, for example sorbitan mono-oleate and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous solution or suspension. This aqueous medium may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1:3 butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 0.10 mg. and about 500 mg. of the active ingredient of the formulae stated above.

From the foregoing formulation discussion it is apparent that the compositions of this invention can be administered orally or parenterally. The term parenteral as used herein includes subcutaneous injection, intraveneous, intramuscular, or intrasternal injection or infusion techniques. In addition, the compounds can be given rectally as suppositories or topically with penetrants.

The following examples are presented to further illustrate the invention.

EXAMPLE 1

3-Allyl-2-iminothiazolidine hydrobromide

A mixture of 1.02 g. of 2-amino-2-thiazoline and 1.4 g. of allyl bromide was refluxed in 15 ml. of isopropanol for 3 hours. After cooling to room temperature, ether was added to incipient cloudiness and the mixture was cooled in the refrigerator overnight. The precipitated 3-allyl-2-iminothiazolidine hydrobromide was collected and dried to give 1.45 g., m.p. 112°–116° C.

Employing the procedure substantially as described in Example 1 but substituting an equimolecular amount of propargyl bromide for the allyl bromide used therein and refluxing for 18 hours, there is produced 2-amino-3-(2-propynyl)thiazolidine, hydrobromide, m.p. 143°–145° C.

EXAMPLE 2

3,5-Dimethyl-2-iminothiazolidine Fumarate

Step A: Preparation of methyl N-(2-hydroxypropyl) dithiocarbamate

40 G (0.242 mmole) of 1-amino-2-propanol oxalate was suspended in 180 ml. of pyridine and 101 g. of triethylamine was added. The mixture was stirred mechanically for 1 hour, there cooled to 0° and 38 g. of carbon disulfide (0.5 mole) was added dropwise. After 2 hours at 0° C., 36 g. of methyl iodide (0.254 mole) was added dropwise and almost all solids dissolved. The mixture was stored in a refrigerator overnight (0°–5° C.). The mixture was poured into 2.4 l. of 3N $H_2SO_4$ and extracted with ether 3 times. The ether extracts were washed with water, 3N $H_2SO_4$, water, aqueous $NaHCO_3$ solution and water, dried over $Na_2SO_4$ and stripped down to 18.79 g. (47%) of oily methyl N-(2-hydroxypropyl) dithiocarbamate.

Step B: Preparation of 5-methyl-2-methylthio-2-thiazoline 17.37 G. of the dithiocarbamate from Step A in 30 ml. dry ether was added to 73 ml. thionyl chloride at 0°–5° C. The mixture was stirred at 0° for 2 hours, then stored in a refrigerator overnight. The thionyl chloride was evaporated at 30° C. and the residual oil (containing elemental sulfur) was poured into saturated $NaHCO_3$ solution and extracted with ether. The etherial fraction was extracted with dilute HCl. The aqueous fraction was basified with NaOH solution and extracted with ether. Evaporation of the ether afforded 6.65 g. liquid residue. This was chromatographed on a column of silica gel using benzene as eluant to give 2.5 g. (16.2%) of oily 5-methyl-2-methylthio-2-thiazoline.

Step C: Preparation of 3,5-Dimethyl-2-methylthio-2-thiazoline fluoborate

588 Mg. of the S-methyl thiazoline from Step B and 592 mg. trimethyl oxonium fluoborate were stirred together in 40 ml. $CH_2Cl_2$ overnight at room temperature. The fluoborate dissolves slowly as it reacts. The reaction mixture was stripped to dryness to give a colorless oil which was used directly in the next step.

Step D: Preparation of 3,5-dimethyl-2-iminothiazolidine fumarate

The crude fluoborate salt from Step C was dissolved in 40 ml. of alcohol and the solution was saturated with gaseous $NH_3$. The solution was stirred at room temperature for 3 hours. The solution was evaporated to dryness. The resulting oily residue was taken up in 10 ml. of water, then 40 ml. $CHCl_3$ was added with stirring and 40% NaOH solution was added to make the aqueous fraction strongly basic. The two layers were separated, and the aqueous fraction was extracted once more with $CHCl_3$. The combined $CHCl_3$ fraction was dried and concentrated to dryness to give 630 mg. of oil. The compound was converted to the fumarate, and crystallized from isopropanol-ether to give 720 mg. cream-colored crystals, m.p. 130°–138° C. (73%) overall. Recrystallization of the fumarate from isopropanol-ether gave 470 mg. 3,5-dimethyl-2-iminothiazolidine fumarate, m.p. 133°–6° C.

EXAMPLE 3

2-Imino-3-methyl-4-trifluoromethyl-4-thiazoline fluorosulfonate 336 mg. of 2-amino-4-trifluoromethylthiazole was dissolved in 15 mg. $CH_2Cl_2$. The flask was placed in an ice bath and 240 mg. of $CH_3SO_3F$ in 5 ml. $CH_2Cl_2$ was added. The mixture was then placed in a refrigerator over the weekend. The colorless crystals were collected on a filter to give 450 mg. (80%) of 2-imino-3-methyl-4-trifluoromethyl-4-thiazoline fluorosulfonate, m.p. 177°–78° C.

EXAMPLE 4

A mixture of 250 parts of 3-methyl-2-iminothiazolidine and 25 parts of lactose is granulated with suitable water, and to this is added 100 parts of maize starch. The mass is passed through a 16-mesh screen. The granules are dried at a temperature below 60° C. The dry granules are passed through a 16-mesh screen and mixed with 3.8 parts of magnesium stearate. They are then compressed into tablets suitable for oral administration.

EXAMPLE 5

A mixture of 50 parts of 3-methyl-2-iminothiazoline, 3 parts of the calcium salt of lignin sulphonic acid, and 237 parts of water is ball-milled until the size of substantially all of the particles is less than 10 microns. The suspension is diluted with a solution containing 3 parts of sodium carboxymethylcellulose and 0.9 part of the butyl ester of p-hydroxybenzoic acid in 300 parts of water. There is thus obtained an aqueous suspension suitable for therapeutic purposes.

EXAMPLE 6

A mixture of 250 parts of the sulfuric acid salt of 3-methyl-2-iminothiazolidine, 200 parts of maize starch and 30 parts of alginic acid is mixed with a sufficient quantity of a 10 percent aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 7

A mixture of 500 parts of 3-methyl-2-iminothiazolidine, 60 parts of maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

What is claimed is:

1. A method of inhibiting indoleamine-N-methyl transferase comprising the administration to a host of a therapeutically effective amount of a compound of formula:

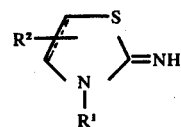

or pharmaceutically acceptable salt thereof, wherein
$R^1$ is $C_{1-2}$ alkyl, $C_3$-alkenyl, or $C_3$-alkynyl; and
$R^2$ is hydrogen, $C_{1-3}$ alkyl or trifluoromethyl.

2. The method of claim 1, wherein the compound is 3-methyl-2-iminothiazolidine.

3. A pharmaceutical composition in unit dosage form for inhibiting indoleamine-N-methyltransferase comprising 5–500 mg. of a compound of formula:

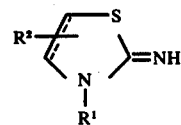

or pharmaceutically acceptable salt thereof, wherein
$R^1$ is $C_{1-2}$ alkyl, $C_3$-alkenyl, or $C_3$alkynyl, and a pharmaceutical carrier.

4. The pharmaceutical composition of claim 3, wherein the compound is 3-methyl-2-iminothiazolidine.

* * * * *